United States Patent [19]  [11] 3,965,178
Johnson et al.  [45] June 22, 1976

[54] METHOD FOR PREPARING TETRABUTYLAMMONIUM BROMIDE

[75] Inventors: Morris A. Johnson; James D. Reedy; Kang Yang, all of Ponca City, Okla.

[73] Assignee: Continental Oil Company, Ponca City, Okla.

[22] Filed: Feb. 12, 1975

[21] Appl. No.: 549,218

Related U.S. Application Data

[63] Continuation-in-part of Ser. Nos. 65,357, Aug. 19, 1973, abandoned, and Ser. No. 401,333, Sept. 27, 1973, abandoned.

[52] U.S. Cl. ............................................ 260/567.6 M
[51] Int. Cl.$^2$ ............................................ C07C 87/30
[58] Field of Search ............................. 260/567.6 M

[56] References Cited
UNITED STATES PATENTS

| | | | |
|---|---|---|---|
| 2,149,379 | 3/1939 | Yabroff et al. | 260/583 N |
| 2,442,457 | 6/1948 | Chanick | 260/583 N |
| 2,569,408 | 9/1951 | de Benneville et al. | 260/567.6 M |
| 3,218,356 | 1/1965 | Melton | 260/567.6 |
| 3,336,196 | 8/1967 | McGregor | 260/567.6 M |
| 3,446,844 | 5/1969 | Carasino | 260/567.6 M |

OTHER PUBLICATIONS

Kittila, R. "Dimethylformamide Chemical Uses" pp. 124–126.

*Primary Examiner*—James O. Thomas, Jr.
*Assistant Examiner*—James H. Reamer
*Attorney, Agent, or Firm*—F. Lindsey Scott

[57] ABSTRACT

Tetrabutylammonium bromide is prepared by mixing n-butylbromide with tributylamine in acetonitrile, in an inert atmosphere, under reflux conditions for a sufficient period of time to form a solution containing tetrabutylammonium bromide, cooling the resulting solution; mixing the solution with water, thus forming a mixture; and recovering tetrabutylammonium bromide in high yield from the mixture.

5 Claims, No Drawings

METHOD FOR PREPARING TETRABUTYLAMMONIUM BROMIDE

REFERENCE TO RELATED APPLICATIONS

This application is a continuation-in-part application of U.S. Ser. No. 65,357, filed Aug. 19, 1970, entitled "Method for Preparing Tetrabutylammonium Bromide," and U.S. Ser. No. 401,333, filed Sept. 27, 1973, of the same title both now abandoned.

FIELD OF THE INVENTION

1. Background of the Invention

This invention relates generally to a process for preparing tetrabutylammonium bromide and more particularly to the production of tetrabutylammonium bromide from n-butylbromide and tributylamine in the presence of acetonitrile.

2. Description of the Prior Art

Electrochemical alkyl lead processes employ tetrabutylammonium bromide (TBAB) as a supporting electrolyte. Unfortunately, this salt is not available in a commercial quantity. A review of the literature indicates that presently known preparative methods are quite unsatisfactory for large-scale preparation.

As compared with TBAB, tetrabutylammonium iodide (TBAI) is much easier to prepare. Utilizing this fact, various authors prepared TBAB from TBAI by treating the latter with $Ag_2O$ and HBr or with AgBr. TBAI has been reacted with AgBr in aqueous solution; subsequent $H_2S$ treatment removed silver ion. The major objection to the above methods is the use of expensive reagents such as iodide and silver ions, which inevitably suffer some loss.

Attempts have also been made to prepare TBAB directly. The reaction of tributylamine with butylbromide at 25°C in the absence of any solvent yielded TBAB melting at 116°–117°C. The yield in this reaction is negligibly small.

SUMMARY OF THE INVENTION

The present invention relates to a process for preparing tetrabutylammonium bromide which comprises:
a. mixing as a solution n-butylbromide and tributylamine in acetonitrile in an inert atmosphere to form a reaction mixture;
b. refluxing the reaction mixture for a period of time sufficient to form a solution containing tetrabutylammonium bromide;
c. cooling the solution;
d. mixing the resulting cooled solution with water to form a mixture;
e. recovering tetrabutylammonium bromide, in high yield, from the mixture.

In a more specific aspect, the aqueous phase is washed with an immiscible organic solvent which has been washed with an aqueous alkali metal hydroxide or ammonium hydroxide solution.

DETAILED DESCRIPTION

By employing the process of the present invention, we have found that tetrabutylammonium bromide can readily be produced in high yields (i.e., in excess of 50 percent). Further, the process can readily be scaled up to a commercial-size operation. In addition, our process has the following advantages over the prior art method of producing tetrabutylammonium bromide.

1. The resulting tetrabutylammonium bromide performs well in electrochemistry, producing a high yield of tetraethyl lead and tetramethyl lead (above 90 percent).
2. Tetrabutylammonium bromide yield is very high (about 50 to about 95 percent in 22 hours).
3. The process can be readily scaled up.
4. No expensive reagents are employed.

In carrying out the reaction of the present invention, the ratio of tributylamine to n-butylbromide is not critical. The reaction occurs in a 1:1 ratio of reactants; however, it is desired to have the n-butylbromide present in about 1 to about 20 mole percent excess, and preferably about 10 percent excess. This excess is desirable to insure that there will be less unreacted tributylamine remaining after the reaction has occurred. Such is desirable because unreacted tributylamine is more difficult to remove from the reaction mixture than is unreacted n-butylbromide. Also, any remaining n-butylbromide has a lesser tendency to interfere with electrochemical reactions in which the tetrabutylammonium bromide is used than does any remaining tributylamine.

In nucleophilic substitution reactions of this type, aprotic dipolar solvents are known to be effective. Some such solvents are acetone, n,n-dimethylformamide, and the like. Such solvents, while suitable, result in low yields when used in the reaction of n-butylbromide and tributylamine to produce tetrabutylammonium bromide.

It has now been found that unexpectedly high reaction yields are obtained when acetonitrile is used as a solvent in the above reaction. Reaction yields in excess of 50 percent based on the limiting reactant, i.e., n-butylbromide or tributylamine, are readily obtained. Yields as high as 75 percent are desirable, and in the preferred embodiments of the present invention, yields in excess of 90 percent are obtained. The amount of acetonitrile employed is not critical as long as there is a sufficient amount to obtain the desired yields. The upper limit is determined by the amount of acetonitrile which reduces the reaction rate to a point which is economically impractical and, in addition, creates the undesirable task of removing this excess amount of solvent prior to recovering the tetrabutylammonium bromide. As a practical matter, the acetonitrile should be present in about 100 to 500 milliliters per mole of tributylamine, and preferably about 200 milliliters per mole.

Once the reaction mixture of n-butylbromide, tributylamine, and acetonitrile has been formed, the reaction mixture is heated to its reflux temperature and maintained at such temperature for an effective period of time to allow the desired reaction to occur. Suitable reaction times are from about 12 to about 24 hours, with preferred reaction times being from about 18 to about 24 hours. Obviously, shorter reaction times can be used if a lesser reaction yield is desired. The reaction is preferably carried out in an oxygen-free atmosphere to prevent oxidation of the tributylamine. Examples of materials suitable for providing this oxygen-free atmosphere are argon, nitrogen, helium, ethylene, and other materials which are oxygen-free and which are inert in the system.

Once the reaction has proceeded to the desired degree of completion, the resulting mixture is cooled. The cooled mixture is then heated to remove the acetonitrile. The residue, containing the desired tetrabutylammonium bromide and any remaining unreacted starting materials, is then admixed with an effective amount of water, thus forming an aqueous layer and an organic layer. It is to be understood that when the reactants are present in substantially stoichiometric quantities and the reaction is substantially complete, there will be substantially no organic layer. The organic materials are removed from the aqueous layer by decanting, washing with an organic solvent, and the like. The aqueous layer, containing the tetrabutylammonium bromide, is then separated from the organic layer, and the tetrabutylammonium bromide is then recovered from the aqueous layer by any suitable means, such as evaporation. When desired, the residue can be evaporated to near dryness and thereafter forming the aqueous solution. Further, it is often desirable to wash the product, which has been recovered, with an effective amount of an immiscible organic solvent prior to forming the aqueous solution. Any suitable immiscible organic solvent which is inert to tetrabutylammonium bromide can be employed. Examples of such solvents are benzene, cyclohexene, and hexane.

The separated aqueous layer is then washed with an effective amount of a wash solvent. The wash solvent can be any suitable organic solvent which can solubilize any unreacted tributylamine and n-butylbromide present and which is also immiscible with or only slightly soluble in water. The organic solvent can be alkyl, alkaryl, or aryl. Some specific examples are benzene, cyclohexene, hexane, and other materials meeting the solubility requirements as set forth above.

The wash solvent described above can be modified, when desired, by contacting the solvent with an aqueous solution containing from about 0.05 to about 50 percent by weight of a basic constituent such as NaOH, KOH, LiOH, and NH$_4$OH. Generally, such aqueous base solution will contain from about 5 to 20 weight percent of the base constituent. Solvent washed in this manner is known as "base washed" solvent.

To better illustrate the process of the present invention, the following examples are given. Example 1 through 5 illustrate the low yields obtained without a solvent or solvents other than acetonitrile, whereas Examples 6 through 9 depict the high yields obtained by the process of the invention.

EXAMPLE 1

A mixture of 30.2 g. butylbromide and 37.1 g. tributylamine was stirred for 26 hours at ambient temperature in a stoppered flask. The reaction mixture was added to 100 ml water, shaken well, and the organic layer was removed. The aqueous solution was washed with three 100-ml aliquots of benzene. A 20-g. portion of the aqueous layer gave only 10 mg oil on evaporation. The organic layer gave only a few mg of yellow oil on evaporation.

EXAMPLE 2

A mixture of 37.07 g. (0.20 mole) of tributylamine, 27.41 g. (0.20 mole) of butylbromide, and 150 ml of acetone was refluxed under a nitrogen atmosphere for 15.5 hours. The reaction mixture was then cooled and mixed with water to form an organic phase and an aqueous phase. The aqueous phase separated from the organic phase and mixed with diethylether to precipitate the product TBAB. The precipitate was washed with diethylether and dried. The reacton yield was 5.4 percent.

EXAMPLE 3

A mixture of 37.07 g. (0.20 mole) of tributylamine, 30.2 g. (0.22 mole) of butylbromide, and 100 ml of n,n-dimethylformamide was refluxed under a nitrogen atmosphere for 21.5 hours. The reaction temperature was maintained below 60°C. The reaction yield was determined as in Example 2 to be 29 percent.

EXAMPLE 4

A mixture of 95.3 g (0.40 mole) of tributylamine, 60.3 g. (0.44 mole) of butylbromide, and 200 ml of n,n-dimethylformamide was refluxed for 22 hours. The reaction temperature was maintained below 60°C. The reaction yield was determined as in Example 2 to be 45 percent.

EXAMPLE 5

A mixture of 60.3 g. butylbromide and 74.1 g. tributylamine was heated while stirring in an 80°–85°C oil bath for 23 hours. The reaction mixture was cooled, added to 400 ml water, and shaken well. The aqueous layer was separated and washed with three 100-ml aliquots of benzene. Yield of TBAB = 4 percent.

The use of some solvents increases TBAB yield. Ethanol and ethyl acetate are often used for this purpose. It has been reported that tributylamine and n-butylbromide, when refluxed for 48 hours in ethyl acetate, produced TBAB in 24 percent yield. The major objection to the use of ethanol and ethyl acetate is that these solvents must be removed very thoroughly from the salt solution. Otherwise, the solvents undergo electrochemical reductions readily and lead to a lower yield of desired electrochemical reduction products, such as TEL and TML. We found that TBAB was prepared in ethanol or isopropanol solvent yielded, on electrolysis, about 5 times more tributylamine than does TBAB solution prepared in acetonitrile. The production of this additional tributylamine lowers the yield of the desired TEL and TML.

We now describe experiments using acetonitrile as a solvent.

EXAMPLE 6

A solution of 60.3 g. n-butylbromide and 74.1 g. tributylamine in 100 ml practical grade acetonitrile was refluxed for 22 hours under argon. The reaction mixture was cooled and then evaporated to near dryness at 30°C. The crystalline mass was dissolved in 100 ml water, and the aqueous solution was washed with three 100-ml aliquots of benzene. TBAB yield = 90 percent.

EXAMPLE 7

A solution of 60.3 g. n-butylbromide and 74.1 g. tributylamine in 100 ml chromatoquality acetonitrile was refluxed for 20 hours under argon. The reaction mixture was cooled and evaporated at 20°–30°C to near dryness. The resulting crystalline mass was washed with 300 ml cyclohexene, dissolved in 100 ml water, and further washed with cyclohexene, and then with 100 ml hexane. TBAB yield = 87 percent.

EXAMPLE 8

A solution of 301 g. butylbromide (2.2 mole) and 371 g. tributylamine (2.0 mole) in 500 ml chromatoquality acetonitrile was refluxed for 22 hours under argon. The reaction mixture was cooled and evaporated to 975 ml (Stock A).

A 300-ml portion of Stock A was evaporated at 20°–30°C to a crystalline slurry. This was washed with three 300-ml aliquots of cyclohexene. The washed crystalline slurry was dissolved in 750 ml water, resulting in an aqueous solution of about 930 ml. Of this aqueous solution, 300 ml was kept; 300 ml was kept under a layer of 100 ml (techn.) n-hexane; and the remaining 330 ml was stored under 100 ml n-hexane. This latter n-hexane was base washed as follows: 1,000 ml technical n-hexane was washed with 350 ml, warm, 20 percent aqueous sodium hydroxide 3 times.

A 300-ml portion of Stock A was evaporated at 40°C to a crystalline slurry which was dissolved in 750 ml water. From this solution, 300 ml was kept; 300 ml was washed with 100 ml n-hexane three times and stored under n-hexane; 350 ml was washed with three 100-ml aliquots of base-washed hexane and stored under an additional 100 ml base-washed hexane.

A 175-ml portion of Stock A was evaporated to a crystalline slurry at 20°–30°C, then 175 ml benzene was added. The salt was dissolved in 440 ml water, the benzene was separated, and the aqueous solution was washed with 3 × 200-ml portions benzene.

The final 175-ml portion of Stock A was reacted as above except the benzene used was from a stock solution prepared by washing 1,000 ml benzene with 4 × 200-ml portions of cold 10 percent sodium hydroxide.

Overall yield of TBAB for this reaction = 89 percent.

EXAMPLE 9

A solution of 60.3 g. n-butylbromide and 64.14 g. tributylamine (0.346 mole) in 200 ml chromatoquality acetonitrile was refluxed for 19 hours under an ethylene atmosphere. The reaction mixture was partially evaporated, then 600 ml diethylether was added to precipitate TBAB. The product was collected on a filter and dried in vacuo at ambient temperature. Yield of TBAB = 86 percent.

After purification, the salt prepared in Examples 3 to 6 was tested as a supporting electrolyte in a TEL and TML process. We found that the use of technical grade n-hexane as a washing agent leads to a poor yield of TEL, when the n-hexane was base washed; however, this difficulty disappeared. When this precaution was taken, all the salt solutions prepared in Examples 3 to 6 gave a high yield of TEL or TML (above 90 percent current efficiency).

Although certain specific examples of the invention have been described as exemplary of its practice, these examples are not intended to limit the invention in any way. Other process parameters and materials may be used in accordance with the broad principles outlined herein, and when so used, are deemed to be circumscribed by the spirit and scope of the invention except as necessarily limited by the appended claims of reasonable equivalents thereof.

What is claimed is:

1. A process for preparing tetrabutylammonium bromide in yields of at least 75 percent based on the amount of tributylamine present, said process comprising mixing as a solution n-butylbromide, tributylamine, and acetonitrile in an inert atmosphere provided by a gas selected from argon, nitrogen, helium, and ethylene to form a reaction mixture wherein said n-butylbromide is present in an amount equal to from about 1.0 to about 1.2 moles per mole of said tributylamine and wherein said acetonitrile is present in an amount equal to from about 100 to about 500 milliliters per mole of said tributylamine, heating said reaction mixture at its reflux temperature for a period of time from about 12 to about 24 hours to form a solution containing tetrabutylammonium bromide; cooling said solution; mixing said solution with water to form a mixture; and recovering said tetrabutylammonium bromide from said mixture.

2. The process of claim 1 wherein said mixture is washed with an organic solvent, said solvent being inert with respect to tetrabutylammonium bromide, substantially immiscible with water and capable of solubilizing unreacted tributylamine and n-butylbromide.

3. The process of claim 2 wherein said solvent is selected from the group consisting of benzene, cyclohexane and hexane.

4. The process of claim 2 wherein said solvent is base washed.

5. The process of claim 2 wherein said n-butylbromide is present in said reaction mixture in a stoichiometric excess of from about 1 to about 10 mole percent excess based on the amount of said tributylamine wherein said time is from about 18 to about 24 hours and wherein said yield is at least 90 percent.

* * * * *